United States Patent [19]

Wilk

[11] Patent Number: 5,257,631
[45] Date of Patent: Nov. 2, 1993

[54] ELECTROCARDIOGRAPHIC METHOD AND DEVICE

[76] Inventor: Peter J. Wilk, 185 W. End Ave., New York, N.Y. 10023

[21] Appl. No.: 917,819

[22] Filed: Jul. 21, 1992

[51] Int. Cl.⁵ .................................. A61B 5/0402
[52] U.S. Cl. ................... 128/710; 128/696; 128/639; 128/644
[58] Field of Search ............... 128/696, 640, 639, 702, 128/710, 708, 706, 644, 384

[56] References Cited

U.S. PATENT DOCUMENTS

| 3,888,240 | 6/1975 | Reinhold, Jr. et al. | 128/696 |
| 4,791,933 | 12/1988 | Asai et al. | 128/696 |
| 4,809,705 | 3/1989 | Ascher | 128/710 |
| 4,858,617 | 8/1989 | Sanders | 128/696 |
| 4,928,690 | 5/1990 | Heilman et al. | 128/696 |
| 5,027,824 | 7/1991 | Dougherty et al. | 128/696 |
| 5,125,412 | 6/1992 | Thornton | 128/710 |

Primary Examiner—William E. Kamm
Assistant Examiner—George Manuel
Attorney, Agent, or Firm—R. Neil Sudol; Henry D. Coleman

[57] ABSTRACT

A device for monitoring heart activity comprises a carrier having a size approximately coextensive with the chest of an adult human being and a plurality of capacitative metallic foil elements attached to the carrier, the foil elements being spaced from each other in an edge-wise direction. A voltage sensing circuit is operatively connected to the foil elements for monitoring voltage levels induced therein upon approximation of the foil elements to a patient's chest.

16 Claims, 1 Drawing Sheet

ELECTROCARDIOGRAPHIC METHOD AND DEVICE

BACKGROUND OF THE INVENTION

This invention relates to a device for monitoring heart activity. More particularly, this invention relates to an electrocardiographic device. This invention also relates to an associated method.

In conventional electrocardiographic techniques, a plurality of leads are attached to the chest of a patient via globs of an electrically conductive gel. Such a technique is time consuming and messy.

OBJECTS OF THE INVENTION

An object of the present invention is to provide an electrocardiographic technique.

Another, more particular, object of the present invention is to provide such a technique which requires less time to implement than conventional techniques.

A further particular object of the present invention is to provide such a technique which is less messy than traditional procedures.

An associated object of the present invention is to provide a device for use in such a method.

These and other objects of the present invention will be apparent from the drawings and detailed descriptions herein.

SUMMARY OF THE INVENTION

A device for monitoring heart activity comprises, in accordance with the present invention, a carrier having a size approximately coextensive with the chest of an adult human being and a plurality of capacitative metallic foil elements attached to the carrier, the foil elements being spaced from each other in an edge-wise direction. A voltage sensing circuit is operatively connected to the foil elements for monitoring voltage levels induced therein upon approximation of the foil elements to a patient's chest.

Preferably, the carrier is substantially planar and made of a flexible material, whereby the carrier may be easily conformed to the surfaces of a patient's chest.

Pursuant to another feature of the present invention, the carrier includes means such as a strap or belt for pressing the foil elements against a patient. Alternatively, the carrier may be provided with a weighted layer, the foil elements being connected to the weighted layer along a major surface thereof. The weighted layer presses the foil elements against the patient under the force of gravity.

Accordingly to one specific embodiment of the present invention, the voltage sensing circuit is connected to the foil elements via a cable. According to an alternative specific embodiment, the voltage sensing circuit is mounted to the carrier, while a transmitter mounted to the carrier serves to transmit encoded voltage signals to a remote receiver.

A display in the form of a CRT tube or a printer is operatively connected to the voltage sensing circuit, e.g., via the transmitter and the receiver, for displaying electrical heart rhythms of the patient.

In a method for monitoring heart activity in accordance with the present invention, a carrier is provided having a size approximately coextensive with the chest of an adult human being, a plurality of capacitative metallic foil elements being attached to the carrier, the foil elements being spaced from each other in an edge-wise direction. The method further comprises the steps of (a) positioning the carrier over a patient's chest to juxtapose the foil elements with predetermined areas of the patient's chest, and (b) automatically monitoring voltage levels induced in the foil elements upon approximation of the foil elements to the patient's chest.

Pursuant to another feature of the present invention, the foil elements are pressed against the patient, for example, by fastening a strap or belt about a rib cage of the patient. Alternatively, a weighted layer may be placed over the foil elements. The weighted layer may be a separate pad or may be incorporated into the foil carrier.

The method may additionally comprise the step of wirelessly transmitting encoded voltage signals to a remote receiver for display or print-out.

An electrocardiographic technique in accordance with the present invention requires less time to implement and is less messy than conventional techniques.

DETAILED DESCRIPTION

Figure 1:
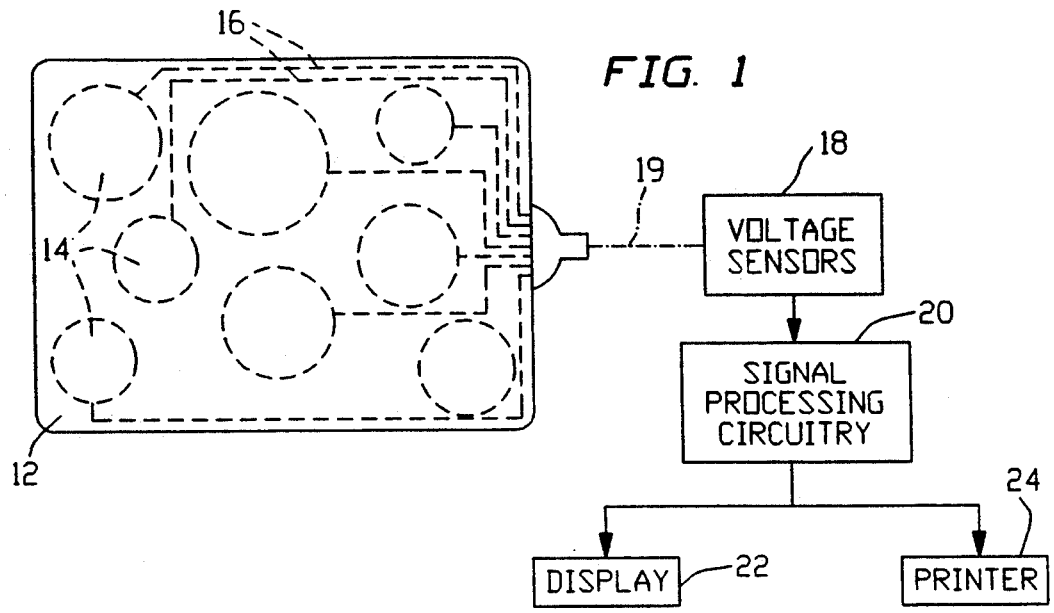
FIG. 1 is partially a schematic top view, on a reduced scale, and partially a block diagram of an electrocardiographic device or apparatus in accordance with the present invention.

As illustrated in FIG. 1, a device or apparatus for electrocardiographically monitoring heart activity comprises a carrier 12 in the form of a pad having a size approximately coextensive with the chest of an adult human being. A lower side or surface of carrier 12 is provided with a plurality of capacitative metallic foil elements 14 which are spaced from each other in an edge-wise direction. Accordingly, in a flat configuration of carrier 12, foil elements 14 are coplanar. A plurality of leads 16 extend from foil elements 14 to a voltage sensing circuit 18 in a cable 19 for monitoring voltage levels induced in the foil elements by electrical potentials on a patient's chest upon approximation of the foil elements to the patient's chest. Voltage sensing circuit 18 is operatively connected to a signal processing circuit 20 which filters out and averages sensed potentials to derive conventional EKG traces which are produced on a CRT display 22 or graphed via a printer 24.

Figure 2:
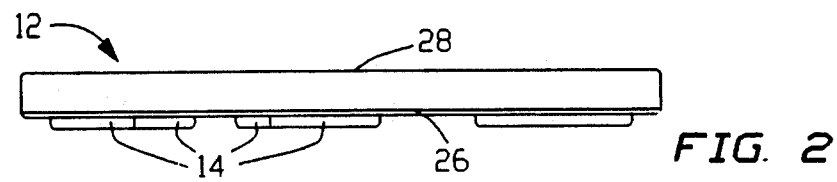
FIG. 2 is a side elevational view of a capacitative foil carrying pad shown in FIG. 1.

Carrier 12 is substantially planar and made of a flexible material, whereby the carrier may be easily conformed to the surfaces of a patient's chest. As illustrated in FIG. 2, carrier 12 includes a base layer 26 of a strong flexible material such as KEVLAR TM or TEFLON TM strands embedded in a polyethylene or polypropylene matrix. On one side of base layer 26 is a weighted layer 28 including a heavy material such as ceramic or metallic particles embedded in a polymeric matrix. Accordingly, weighted layer 28 is also flexible, enabling carrier 12 to conform to a person's chest surfaces and thereby place foil elements 44 in close juxtaposition to the patient's skin.

Depending on the sensitivity of foil elements 14 and voltage sensing circuit 18, carrier 12 may be disposed over a person's clothing. A thin protective layer (not illustrated) may be provided over foil elements 14 for maintaining the integrity thereof.

Figure 3:
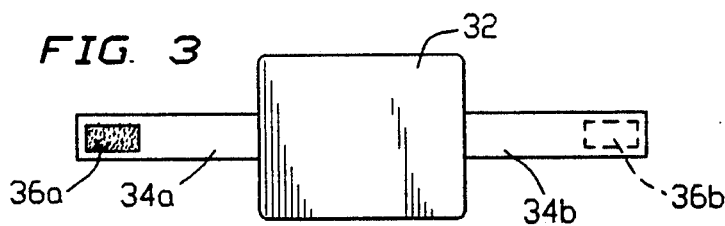
FIG. 3 is a schematic top view, on a substantially reduced scale, of a modified electrocardiographic device or apparatus in accordance with the present invention.

As illustrated in FIG. 3, a pad 32 which carries a plurality of capacitive foil patches (not shown) and is provided with straps or belts 34, 34b for attaching pad 32 about a patient's chest. Straps or belts 34, 34b are provided with hook and loop (VELCRO) type fasteners 36a, 36b for ensuring a tight fit to thereby press the foil patches against the patient.

Figure 4:
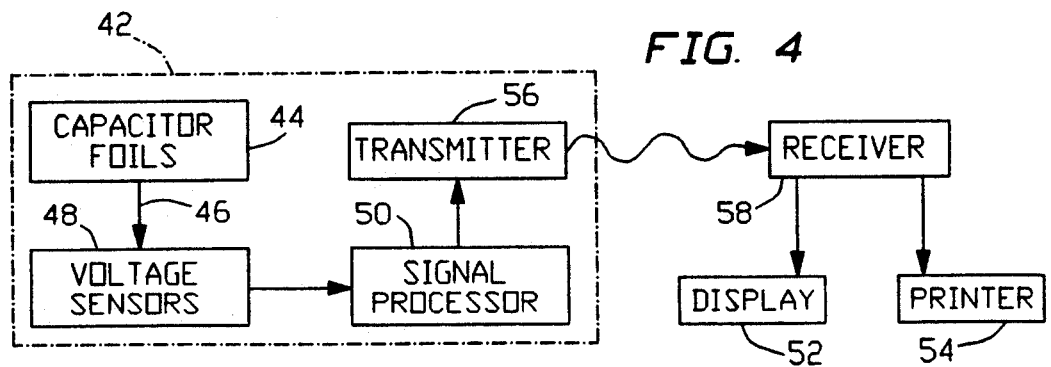
FIG. 4 is a block diagram of yet another electrocardiographic device or apparatus in accordance with the present invention.

As depicted in FIG. 4, another device or apparatus for electrocardiographically monitoring heart activity comprises a carrier 42 in the form of a chest-size pad. A lower side or surface of carrier 42 is provided with a plurality of capacitive metallic foil elements 44 which are edge-wise or laterally spaced from each other. Leads 46 extend from foil elements 44 to a voltage sensing circuit 48 disposed on carrier or pad 42. Circuit 48 monitors voltage levels induced in foil elements 44 by electrical potentials on a patient's chest upon positioning of carrier or pad 42 to juxtapose foil elements 44 to the patient's chest. Voltage sensing circuit 48 is operatively connected to a signal processing circuit 50 also disposed on carrier or pad 42. Circuit 50 filters out and averages sensed potentials to derive conventional EKG traces which are reproducable on a CRT display 52 or via a printer 54. The derived EKG traces are encoded by processing circuit 50 and transmitted wirelessly from a transmitter 56 on carrier or pad 42 to a receiver 58 at a remote, stationary location. Receiver 58 is connected to CRT display 52 and printer 54.

Accordingly to one specific embodiment of the present invention, the voltage sensing circuit is connected to the foil elements via a cable. According to an alternative specific embodiment, the voltage sensing circuit is mounted to the carrier, while a transmitter mounted to the carrier serves to transmit encoded voltage signals to a remote receiver.

To electrocardiographically monitor heart activity in a patient, carrier 12 or 42 is positioned over the patient's chest to juxtapose foil elements 14 or 44 with predetermined areas of the patient's chest. Carrier 12 or 42, and consequently foil elements 14 or 44, are pressed to the chest surface, either directly or through a clothing layer. Voltage levels induced in foil elements 14 or 44 are automatically monitored by voltage sensing circuit 18 or 48 upon juxtaposition of the foil elements to the patient's chest.

Although the invention has been described in terms of particular embodiments and applications, one of ordinary skill in the art, in light of this teaching, can generate additional embodiments and modifications without departing from the spirit of or exceeding the scope of the claimed invention. For example, the shapes and sizes of foil elements 14 and 42 are variable to maximize the collection of appropriate data on electrical potentials.

Accordingly, it is to be understood that the drawings and descriptions herein are proferred by way of example to facilitate comprehension of the invention and should not be construed to limit the scope thereof.

What is claimed is:

1. A device for monitoring heart activity, comprising:
    capacitive coupling means including a plurality of capactitative metallic foil elements for detecting EKG signals, said foil elements being sufficiently large in area to detect voltage potentials through a clothing layer over a person's chest and being spaced from each other in an edge-wise direction;
    carrier means for attaching said foil elements to one another and maintaining said elements in spaced relation to each other, said carrier means having a size approximately coextensive with the chest of an adult human being; and
    voltage sensing means operatively connected to said foil elements for monitoring voltage levels induced therein upon approximation of said foil elements to a patient's chest.

2. The device defined in claim 1 wherein said carrier includes means for pressing said foil elements against a patient.

3. The device defined in claim 2 wherein said means for pressing includes a strap or belt.

4. The device defined in claim 2 wherein said means for pressing includes a weighted layer of said carrier, said foil elements being connected to said weighted layer along a major surface thereof.

5. The device defined in claim 1, further comprising display means operatively connected to said voltage sensing means for displaying electrical heart rhythms of the patient.

6. The device defined in claim 5 wherein said display means includes a CRT monitor.

7. The device defined in claim 5 wherein said display means includes a printer.

8. The device defined in claim 1 wherein said voltage sensing means is mounted to said carrier, further comprising transmitter means mounted to said carrier for wirelessly transmitting encoded voltage signals to a remote receiver.

9. The device defined in claim 8, further comprising display means operatively connected to said voltage sensing means via said transmitter means and said receiver for displaying electrical heart rhythms of the patient.

10. The device defined in claim 1 wherein said voltage sensing means is connected to said foil elements via a cable.

11. A method for monitoring heart activity, comprising the steps of:
    providing a carrier having a size approximately coextensive with the chest of an adult human being, capacitative coupling means including a plurality a plurality of capacitative metallic foil elements for detecting EKG signals being attached to said carrier, said foil elements being sufficiently large in area to detect voltage potentials through a clothing layer over a persons's chest and being spaced from each other in an edge-wise direction;
    positioning said carrier over a layer of clothing on a patient's chest to juxtapose said foil elements with predetermined areas of the patient's chest; and
    automatically monitoring voltage levels induced in said foil elements upon approximation of said foil elements to the patient's chest.

12. The method defined in claim 11, further comprising the step of pressing said foil elements against the patient.

13. The method defined in claim 12 wherein said step of pressing includes the step of disposing a weighted layer above said foil elements.

14. The method defined in claim 13 wherein said layer is a part of said carrier.

15. The method defined in claim 12 wherein said step of pressing includes the step of fastening a strap or belt about a rib cage of the patient.

16. The method defined in claim 11, further comprising the step of wirelessly transmitting encoded voltage signals to a remote receiver.

* * * * *